United States Patent [19]

Hardie

[11] Patent Number: 4,477,432

[45] Date of Patent: Oct. 16, 1984

[54] ORAL IMMUNE GLOBULIN

[75] Inventor: W. Richard Hardie, Walnut Creek, Calif.

[73] Assignee: Cutter Laboratories, Inc., Berkeley, Calif.

[21] Appl. No.: 365,759

[22] Filed: Apr. 5, 1982

Related U.S. Application Data

[63] Continuation-in-part of Ser. No. 259,758, May 1, 1981, abandoned.

[51] Int. Cl.³ .............................................. A61K 45/00
[52] U.S. Cl. ....................................... 424/85; 424/86; 424/87; 424/176; 424/177
[58] Field of Search .............................. 424/85, 86, 87

[56] References Cited

U.S. PATENT DOCUMENTS 4,335,099  6/1982  Funakoshi et al. .................... 424/85

OTHER PUBLICATIONS

Blum et al—Pediatr. Res., vol. 15, (1981), pp. 1256–1260.
Petersen et al—Quarterly Rev. Allergy & Applied Immunol., vol. 10, No. 2, (1956), pp. 185–186.

*Primary Examiner*—Sam Rosen
*Attorney, Agent, or Firm*—David J. Aston; Lester E. Johnson; Theodore J. Leitereg

[57] ABSTRACT

There is disclosed an oral pharmaceutical composition for therapeutic use comprising a therapeutically effective amount of orally administerable immune globulin in a pharmaceutically acceptable carrier.

3 Claims, No Drawings

ORAL IMMUNE GLOBULIN

CROSS-REFERENCE TO RELATED APPLICATIONS

This is a continuation-in-part of U.S. patent application Ser. No. 259,758 filed May 1, 1981, now abandoned.

BACKGROUND OF THE INVENTION

1. Field of the Invention

This invention relates to and has among its objects provision of novel immunizing agents. Further objects of the invention will be evident from the following description wherein parts and percentages are by weight unless otherwise specified.

2. Description of the Prior Art

The importance of the humoral defense system, immune globulin (IG) has long been recognized. IG preparations for therapeutic use have been available for about 30 years, however, the structure and function of IG ("gamma globulins") has only been understood in detail for a few years. Five classes of immunoglobulins are now recognized: IgA, IgG, IgM, IgE and IgD. The functions of the first four classes have been extensively researched, whereas the clinical significance of IgD is still essentially unknown. The bulk of the serum immunoglobulins (approximately 70%) are IgG, and they are the carriers of many of the body's acquired defensive functions. Like the other forms of IG, the IgG molecule consists of heavy and light polypeptide chains. Proteolytic enzymes can be used to split IgG into various fragments, called Fc, Fd and Fab fragments. For the immunoglobulin molecule to be fully functional and hence therapeutically effective, it is believed that its molecular integrity, particularly its primary or tertiary molecular structure, must be retained or, if not, its function would be impaired.

Intramuscularly injectable (IM) and intravenously injectable (IV) immune globulin preparations for parenteral administration are known. The IVIG material contains either a modified or unmodified IG molecule or both.

It has been observed that breast-fed newborn infants are better protected against gastrointestinal infection than are formula-fed infants. (Jelliffe, *Amer. J. Clin. Nutr.*, 29, 1227, 1976; Kleinman et al., *Digestive Diseases and S.C.*, 24 (11):876:82, 1979; Beer et al., *J. Invest. Dermat.*, 63:55–74, 1974; Ammann et al., Soc. for Exp. Biol. and Med., 122:1098–1101, 1966; Lourguia et al., *Arch. Argent. Pediat.*, 72:109–125, 1974; Hilper et al., "Food and Immunology", Hambraeus L., Hanson L. A., McFarlane H. (Eds) pp. 182–196, 1977; Hanebery et al., *Eur. J. Pediatr.*, 132:239, 1979). This can be accounted for by the presence of T and B lymphocytes, phagocytes, antibodies, complement components and other anti-bacterial substances such as lactoferrin and lysozyme. The relative importance of these elements in milk is difficult to assess although removal of cells by heating or centrifugation may lead to a significant loss in protective ability (Pitt et al., *Ped. Res.*, 11, 906, 1977).

U.S. Pat. No. 4,096,244 describes a dried particulate porcine or bovine blood serum containing immunoglobulins which is acceptable to and palatable to newborn piglets when orally administered to piglets as a feed stuff component.

In U.S. Pat. No. 3,975,517 a method is described wherein cows are vaccinated with a particular vaccine for coliform enteritis. Recovered milk from the so-vaccinated cows can be orally fed to newborn calves on a continuous basis.

An immune milk product containing antibodies is disclosed in U.S. Pat. No. 3,911,108 and may be administered to baby pigs to protect against transmissible gastroenteritis.

Milk obtained from milk-bearing animals which have been treated with a specific mixed bacterin vaccine is described in U.S. Pat. No. 3,128,230. The milk may be administered to human and lower animals for treatment of various diseases.

In U.S. Pat. No. 2,607,716 there is disclosed a composition for preventing or inhibiting scours in calves, lambs, goats, pigs, rabbits, and the like. Plasma, serum, or globulin fraction of pooled blood from dairy cattle, sheep, or pigs containing immune proteins is spray-on freeze-dried and mixed with a solid Vitamin K source and partially digested milk solids. In use the mixture is mixed with water and orally administered to the animal to be treated.

SUMMARY OF THE INVENTION

It has been found that human IG may be administered orally with significant maintenance of molecular integrity. This result is surprising because degradation of the IG molecule would be anticipated to occur in the stomach by analogy with the ready degradation observed with various enzymes in vitro. As mentioned above, integrity of the IG molecule is believed to be required for therapeutic effectiveness.

The product of the present invention is an oral pharmaceutical composition for therapeutic use comprising a therapeutically effective amount of orally administerable human blood fractionation derived immune globulin in a pharmaceutically acceptable carrier.

Oral administration of IG has advantages over parenteral administration. A primary advantage is the avoidance of injection, either intramuscularly or intravenously, as a means of administration and the discomforts, etc., associated therewith. An oral IG composition provides ease of administration and avoids the pain associated with parenteral administration, particularly intramuscular. Larger doses of IG may be administered orally than parenterally.

DESCRIPTION OF THE PREFERRED EMBODIMENTS

The oral pharmaceutical composition of the invention comprises orally administerable hepatitis-safe immune serum globulin in a therapeutically effective amount in a pharmaceutically acceptable carrier. The immune globulin can be prepared from human blood by fractionation in the same manner in which material intended for parenteral, i.e., intramuscular (IMIG) or intravenous (IVIG) use is prepared. IMIG and IVIG are well known and can be prepared by known means. For example, IMIG is commonly prepared by Cohn fractionation (Cohn et al., *J. Am. Chem. Soc.*, 68, 459–475 [1946]; Oncley et al., *J. Am. Chem. Soc.*, 71, 541–550 [1949]). IVIG can be prepared by a number of methods such as ultracentrifugation (Barundern et al., *Vox Sang.*, 7, 157–174 [1962]), pH adjustments (Koblet et al., *Vox Sang.*, 13, 93–102 [1967]), careful fractionation (Schneider et al., *Vox Sang.*, 31, 141–151 [1976]), enzymatic modification (Fahey et al., *J. Exper. Med.*, 118, 845–868 [1963]; Kneapler et al., *Vox Sang.*, 32, 159-164 [1977]), structural modification (Barundern et al., *Monogr. Allergy,* 9, 39-60 [1975]), chemical modification (Stephan, *Vox Sang.,* 28, 422-437 [1975]; Masuko et al., *Vox Sang.,* 32, 175-181 [1977]), and reduction and alkylation (Pappenhagen et al., U.S. Pat. No. 3,903,262).

Other methods of fractionation to yield IG which may be used include polyelectrolyte affinity adsorption, large scale electrophoresis such as disclosed in U.S. Pat. No. 4,246,085, ion exchange adsorption, polyethylene glycol fractionation, and so forth. However, any method which fractionates an immune serum globulin comprising IgG from a human source may be used in the present invention. The specific disclosures of the above publications and patents are incorporated herein by reference thereto.

As the pharmaceutically acceptable carrier in accordance with the invention one may use liquid, semi-solid, e.g., pastes, or solid carriers. Particular requirements of the carrier are that it not be harmful to the recipient, that the IG be stable therein, and that the carrier not be detrimental to the IG. The IG may be combined with the carrier by solution, suspension, emulsification, admixture, encapsulation, absorption, adsorption and the like. Examples of carriers which may be used in the present invention are, by way of example and not limitation, water, fats, oils, lipids, liposomes, resins, binders, fillers, and the like, or combinations thereof. In some compositions a lubricant or disintegrator may be present. An important preferred characteristic of a carrier suitable in the present composition is that it protect the therapeutic effectiveness of the IG, by e.g., maintaining the integrity of the IG molecule or the activity thereof and that it facilitate delivery of active IG to the site whereat the therapeutic activity of the IG is required. By the term therapeutic effectiveness is meant that the oral composition be effective for the preventative or curative health measure for which it is orally administered similar to that for parenterally administered IG.

The oral composition of the invention may contain a stabilizing agent which protects the IG from loss of therapeutic activity by denaturation and the like. As the stabilizing agent one may use buffers, amino acids such as glycine, lysine, etc., carbohydrates such as dextrose, mannose, galactose, fructose, lactose, sucrose, maltose, sorbitol, mannitol, etc., proteolytic enzyme inhibitors, and so forth, or combinations thereof, in an amount sufficient to stabilize the IG in the oral composition. Also for consideration is the conjunctive use of a carrier and stabilizer to achieve the aforementioned stabilization and protective effects and controlled release preparations.

The instant product when used to treat enteric infections might also contain a bulking material such as cellulose or methylcellulose in amounts conventional in the art, e.g., about one to two grams per 100 ml.

Furthermore the present composition many contain an agent that stabilizes the immuno globulin in the digestive tract or an antidiarrheal agent such as an opium, an adsorbent powder, or an anticholinergic. Opiums useful in the invention, which are also antispasmodics (decrease time out of bowel) include codeine phosphate (dosage of 15-60 mg every six hours), diphenyloxylate (5 mg every six hours), and mepeverine. An example of an adsorbent powder would be kaolin (1-2 g every four hours).

Suitable anticholinergics are, for example, atropine (0.5-0.1 mg every 6-8 hours) and propantheline (75 mg daily in divided doses).

The product of the invention may contain an antacid, which may be administered every four to six hours, such as sodium bicarbonate (4.4 g), magnesium oxide or hydroxide (5.9 g), calcium carbonate (4.5 g), magnesium trisilicate (50 g), magnesium carbonate (63 g), and aluminum hydroxide gel (715 ml).

The above dosages are based on current usage of the above drugs individually or in combination. The amounts of the drugs used in an oral product of the invention would be that necessary to achieve the desired results, e.g., in an antacid amount or in an anticholinergic amount. This is easily ascertained by one skilled in the art using the above guidelines. Of course, the added agent must not be detrimental to the activity of the immune globulin.

The IG should be present in the oral composition of this invention in a therapeutically effective amount. The amount of IG should, therefore, be that which will render the oral composition therapeutically active for the particular prophylactic or curative effect desired. Generally, the instant oral composition will contain about 1-80% IG, preferably about 5-50% of which not less than 70% is gamma globulin (IgG) as mentioned above. The product may contain other globulins such as IgA, IgM, IgD, and IgE. For example, Cohn Fraction II+III contains the following proportions of the above: about 8 parts IgG to 1 part each of IgA and IgM and traces of IgD and IgE.

The pH of the oral composition should be pharmaceutically acceptable and not result in destabilization of the composition. The pH of the composition should therefore be adjusted, where necessary, to within the range of about 4-8, preferably about 6-7, by addition thereto of a pharmaceutically acceptable acid or base.

It may be desirable for purposes of the invention to incorporate into the oral composition certain flavoring agents to enhance its palatability. A preferred additive for this purpose is sorbitol. However, the flavoring agent may be selected from a number of known agents and may be mixed with the oral composition in an amount sufficient to render the oral composition palatable. Generally, the flavoring agent is present in the oral composition in an amount of about 1-20%; however, flavoring agents such as vanilla, strawberry, cherry, and the like are usually present at a level of less than 1%.

A typical formulation of an oral pharmaceutical composition in accordance with the invention is, by way of example and not limitation, an aqueous solution having the following composition:

| | |
|---|---|
| IG concentration | 5-20 g/100 ml. |
| pH | 6-7 |
| Sterility, pyrogenicity, safety | pharmaceutically acceptable |
| Purity of IG | NLT* 90% Gamma Globulin |
| Carbohydrate such as dextrose, maltose, sorbitol | 1-20 g/100 ml. |

*NLT = Not less than

The starting material for the above formulation is the globulin fraction isolated from human blood plasma by Cohn fractionation (Cohn et al., ibid.), which is known to be hepatitis-safe. (Cohn Fraction II+III paste, the hepatitis safety of which is not known, may be rendered so by methods known in the art such as by heat pasteurization in the presence of a stabilizer.) Dry Immune Globulin (Human) or Cohn Fraction II paste is suspended in a carbohydrate solution such that its protein concentration is 5–20%. The temperature of the suspension is maintained at not more than 5° C. The solution pH value is adjusted to about 6–7 by addition of a pharmaceutically acceptable acid or base, and the solution is clarified. The solution is sterile filtered and filled into appropriate bottles. Each bottle contains 1.0 gram of protein and 0.5 gram of carbohydrate. The final container bottles are plug frozen, lyophilized, and stored at 2° to 8° C.

ORAL ADMINISTRATION OF IG

Patients and protocol—Seven thriving formula-fed 4–13 week old immature infants (birth weight 0.86–1.46 kg.; weight at study 1.36–1.7 kg.) were selected from a transitional nursery population. None received breast milk in the two weeks prior to this study. A modified immune globulin (MIG) prepared according to U.S. Pat. Nos. 3,903,262 and 4,186,192 in doses of from 1–8 ml/kg/day in divided doses was administered orally in formula feedings for 5 consecutive days to six infants. One infant served as control. All stools were collected and saved for each 24 hour period beginning with the day before MIG feedings began and continuing for 2 days after they ended. The samples were then frozen at −20° C. for later determinations of immunoglobulin content and opsonic activity.

Coproantibodies—The frozen stool samples were quantitatively removed from the diapers, lyophylized, ground into powder and weighed. Ten ml. of phosphate buffered saline (pH 7.2) was added for each gram of dried stool, mixed for 30 minutes at room temperature and then spun at $20,000 \times g$ at 4° C. for 30 minutes. The supernatant was removed, sterile filtered, and stored at −70° C. until needed. Quantitative immunoglobulin G, A and M levels on these samples were performed by radial immunodiffusion (Meloy Laboratories, Springfield, VA. and Kallestad Laboratories, Chaska, Minn.). Immunoelectrophoresis was performed according to the method of Scheidegger, *Int. Arch. Allergy,* 7, 103 (1955) with MIG or stool extract in the wells. After 2 hours in the chamber, antisera to IgG, IgA, and IgM were added to the troughs.

Opsonic activity as measured by neutrophil chemiluminescence—The MIG employed contained high antibody titer to Group B streptococcus and this organism was chosen as the target for opsonization. Type III Group B streptococcus (SS-893, supplied by the Communicable Disease Center, Atlanta, Ga.) was prepared and standardized according to the method of Hemming et al., *J. Clin. Invest.,* 58, 1379 (1976).

The Group B streptococci were opsonized by mixing 0.4 cc. with 0.1 cc. of stool extract and rotating for 40 minutes at 37° C. The organisms were then washed twice in phosphate buffered saline, centrifuged and diluted to original volume before being used immediately in the chemiluminescence assay.

Chemiluminescence (CL) was performed in a liquid scintillation counter (Beckman LS 8000) in the single photon count mode with the reaction mixtures containing 0.7 cc. of PMN ($2.5 \times 10^6$/cc.) and 0.3 cc. of opsonized Group B Streptococci ($5 \times 10^8$ to $1 \times 10^9$ colony forming units/ml.). All reaction vials were kept at 37° C. in a Dubnoff shaking water bath and removed only for the brief time required for counting.

Clinical observations—No adverse effects of the oral MIG feedings were noted during the course of the study. There was no increased regurgitation of feedings, diarrhea, or other alteration in stool pattern. All infants remained clinically well and continued to gain weight.

Stool Immunoglobulins—The MIG employed contained 14 mg/dl. of IgG. Trace quantities of both IgM and IgA immunoglobulins were found in all stool samples, including the control samples collected on each infant before and after the MIG feedings and in the control infant not given MIG. Levels of IgM and IgA did not rise during the MIG feedings.

No infant had measurable IgG in 24 hours stool samples collected before initiation of immunoglobulin feedings, further, in each case, the stool IgG levels declined to negligible amounts within 48 hours after the last feeding. IgG was found in the stools of all six infants fed MIG. This IgG ranged from 3 to 72 mg/24 hours and represents 4–12% of the oral dose. Increasing doses of oral MIG were associated with higher amounts of IgG excreted per day, suggesting a linear relationship between the amount ingested and the amount recovered.

Opsonic studies—Normal granulocytes ($1.75 \times 10^6$) were mixed with Group B streptococcus exposed to saline, MIG or stool supernatants from an MIG-fed infant and the chemiluminescence produced is measured over time. The peak response in cpm per $2 \times 10^6$ cells is used as an index of opsonic activity. This is generally reached at seven minutes after addition of PMNs to the reaction vial. There was then a rapid fall-off in counts over the subsequent 21 minutes. The curves for MIG, stools, and saline are similar in configuration, except for the peak CL achieved.

Stool samples with IgG levels greater than 100 mg/dl. uniformly supported chemiluminescence (CL) and were effective opsonins for Group B streptococcus at titers ranging up to 1/8 or 1/16. Stool samples with IgG levels less than 100 mg/dl. did not opsonize Type III Group B streptococcus and therefore were poorly supportive of CL. This was also true for stools from the control infant as well as for all stool samples collected prior to MIG feedings and 48 hours after MIG feedings.

With respect to CL counts and their relationship to stool IgG levels, intensity of CL response did not relate to the IgG level in a linear fashion. With respect to chemiluminescence response on stool samples with antibody levels both above and below 100 mg/dl., on undiluted MIG and on saline controls, the average CL counts of those samples with coproantibody levels in excess of 100 mg/dl. was $69 \times 10^3$ compared with $69 \times 10^3$ for samples with levels less than 100 ml/dl. The difference was highly significant ($p < 0.001$).

The difference between the high IgG samples and the saline controls ($40 \times 10^3$) was also highly significant ($p < 0.001$) as was that between MIG and saline controls ($p < 0.001$). No statistical difference in CL was found between saline controls and samples with less than 100 mg/dl. of IgG or between samples with greater than 100 mg/dl. of IgG and MIG.

In studies employing a rabbit ileal loop model, Zinkernagel et al., in *Med. Microbiol. Immunol.,* 162, 1 (1975) showed that passive immunization with, i.e., injection into a loop of rabbit intestine of bovine immunoglobulin (50 mg. of IgG per loop) was effective in decreasing viability of several strains of human enterophathogenic *E. coli.*

The above infant study demonstrates that the infants stool contained significant quantities of undigested and intact IgG and that this coproantibody retained significant opsonic activity for Type III Group B Streptococci. Oral IG, therefore, may be used in prevention or treatment of enteric infections, e.g., *E. coli, V. cholera, S. typhosa* or intoxications, e.g. infantile botulism, since intact IgG with opsonic activity persisted in the gastrointestinal tract and thus is available to function in such prevention or treatment.

What is claimed is:

1. A method of prevention or treatment of enteric infections in humans which comprises orally administering to a patient a composition comprising an oral pharmaceutical composition having therapeutic effectiveness toward enteric infections containing in a pharmaceutically acceptable carrier about 5–20% by weight of an orally administerable hepatitis-safe, human blood fractionation derived immune globulin containing not less than 70% IgG by weight and about 1–20% by weight of a carbohydrate and having a pH of about 4–8.

2. The method of claim 1 wherein the carrier is water.

3. The method of claim 1 wherein the carrier is selected from the group consisting of fats, oils, lipids, waxes, liposomes, resins, binders, and fillers.